United States Patent [19]

Zerbes et al.

[11] Patent Number: 4,720,549

[45] Date of Patent: Jan. 19, 1988

[54] PROCESS FOR THE PREPARATION OF IMIDAZOLYL-METHANE DERIVATIVES

[75] Inventors: Rudolf Zerbes; Erik Regel, both of Wuppertal, Fed. Rep. of Germany

[73] Assignee: Bayer Aktiengesellschaft, Leverkusen, Fed. Rep. of Germany

[21] Appl. No.: 923,535

[22] Filed: Oct. 27, 1986

[30] Foreign Application Priority Data

Nov. 2, 1985 [DE] Fed. Rep. of Germany ....... 3538873

[51] Int. Cl.$^4$ .......................................... C07D 233/54
[52] U.S. Cl. .................................... 548/335; 548/345
[58] Field of Search ............................... 548/345, 335

[56] References Cited

PUBLICATIONS

Houben-Weyl, Methoden der Organischen Chemie, 4th Ed., vol. 11/1, p. 643. (1957).

*Primary Examiner*—Henry R. Jiles
*Assistant Examiner*—Robert C. Whittenbaugh

*Attorney, Agent, or Firm*—Sprung Horn Kramer & Woods

[57] ABSTRACT

Imidazolyl-methane derivatives of the formula

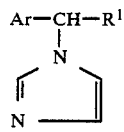

where Ar is an optionally substituted phenyl and $R^1$ is alkyl or optionally substituted phenyl is prepared by reaction of a ketone of the formula

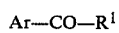

in which Ar and $R^1$ have the abovementioned meanings is reacted with imidazole in the presence of formic acid.

9 Claims, No Drawings

PROCESS FOR THE PREPARATION OF IMIDAZOLYL-METHANE DERIVATIVES

The present invention relates to a new process for the preparation of known imidazolyl-methane derivatives, which have antimycotic properties.

It has already become known that imidazolyl-methane derivatives are obtained when carbinols are either reacted with thionyl-bis-imidazole; or first halogenated in a conventional manner, and subsequently reacted with imidazole, if appropriate in the presence of an acid acceptor and in the presence of an inert organic solvent (cf. in this respect DE-OS (German Published Specification) No. 2,461,406, DE-OS (German Published Specification) No. 2,130,673 and DE-CS (German Published Specification) No. 2,418,502).

These processes either have the disadvantage of being multiple stage processes (ketone derivative →hydroxy derivative →halo derivative →final product) or the preparation of thionyl-bis-imidazole being necessary. Both lead to unsatisfactory space/time yields or to high preparation costs.

It is also known that amines can be reductively alkylated in good yield with ketones in the presence of formic acid (Leuckart-Wallach reaction; cf. in this respect, for example, Houben-Weyl, Methoden der Organischen Chemie [Methods of Organic Chemistry], 4th edition, volume 11/1, page 643 (1957); Methodicum Chimicum, volume 6, page 536 et seq. (1974); or Org. Reactions 5, 301 (1949)). However, corresponding reactions using unsaturated heterocycles have not yet been described.

It has now been found that the known imidazolyl-methane derivatives of the formula (I)

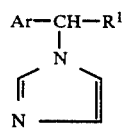

in which

Ar represents optionally substituted phenyl and
$R^1$ represents alkyl or optionally substituted phenyl,
are obtained when ketones of the formula (II)

$$Ar-CO-R^1 \quad (II)$$

in which

Ar and $R^1$ have the abovementioned meaning,
are reacted with imidazole in the presence of formic acid.

It can be described as surprising that the process according to the invention supplies the compounds of the formula (I) in good yields, since imidazole is not an amine in the narrowest sense. As well as this, imidazole has a low basicity relative to the saturated heterocyclic amines described in the literature. In addition, imidazole is a sterically demanding compound, which should lead to considerable difficulties in the reaction with ketones of the formula (II) also having sterically demanding substituents, such as, for example, Ar=biphenyl and $R^1$=phenyl. Thus, ketones of the benzophenone type have also not been employed hitherto in Leuckart-Wallach reactions.

The process according to the invention is distinguished by a number of advantages. Thus, it is a simple, single-stage process which leads to good yields. The compounds required as starting materials are cheap base chemicals.

If, for example, 4-benzoylbiphenyl is used as starting material, then the course of the process according to the invention can be illustrated by means of the following reaction diagram:

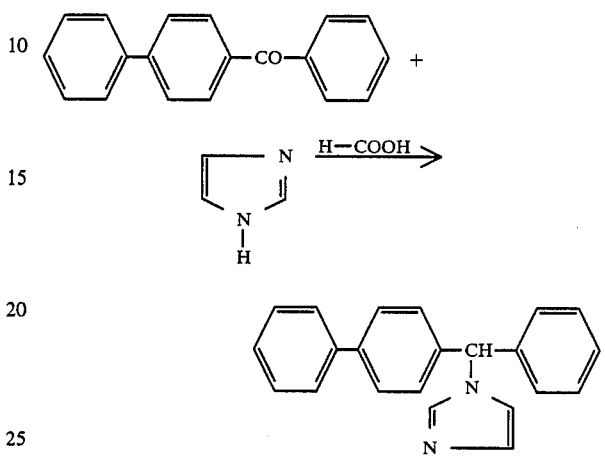

The ketones to be used as starting materials in the process according to the invention are generally defined by the formula (II). In this formula, Ar preferably represents optionally singly to triply, identically or differently substituted phenyl, substituents which may be mentioned being: alkyl and halogen, and phenyl, phenoxy and phenylthio which are, in each case, optionally substituted by halogen or alkyl. $R^1$ preferably represents straight-chain or branched alkyl having up to 6 carbon atoms and optionally singly to triply, identically or differently substituted phenyl, substituents which may be mentioned being: halogen, alkyl and haloalkyl.

Particularly preferred starting materials are those compounds of the formula (II) in which Ar represents phenyl which is optionally substituted by fluorine, chlorine, methyl, ethyl, phenyl, chlorophenyl, phenoxy or chlorophenoxy and $R^1$ represents methyl, ethyl, n-propyl, i-propyl, n-butyl, tert.-butyl and phenyl which is optionally substituted by fluorine, chlorine, methyl or trifluoromethyl.

Starting materials of the formula (II) in which

Ar represents phenyl which is optionally substituted by chlorine or phenyl and $R^1$ represents methyl or phenyl which is optionally substituted by chlorine are very particularly preferred.

The ketones of the formula (II) are generally known compounds of organic chemistry.

The reaction temperatures can be varied within a relatively wide range when the process according to the invention is carried out. In general, temperatures between 100° C. and 250° C., preferably between 150° C. and 200° C. are employed.

On carrying out the process according to the invention, 4 to 12 moles, preferably 6 to 10 moles, of imidazole and 10 to 50 moles, preferably 20 to 40 moles, of formic acid are, in general, employed per mole of ketone of the formula (II).

It has in many cases proven advantageous to work in the presence of an acidic catalyst, such as, for example, sulphuric acid or p-toluenesulphonic acid.

The final products of the formula (I) are isolated in a generally conventional and known fashion.

The imidazolyl-methane derivatives of the formula (I) which can be prepared by the process according to the invention are known (cf. German Published Specifications Nos. 2,130,673, 2,418,502 and 2,461,406). They are distinguished by means of very good antimycotic properties.

The process according to the invention is illustrated by means of the following examples.

EXAMPLE 1

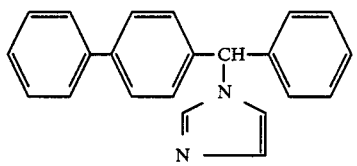

According to the invention 64.5 g (0.25 mol) of 4-benzoylbiphenyl, 136 g (2.0 moles) of imidazole and 1.25 g of -p-toluenesulphonic acid are heated to 180° C. A total of 36 g (8.0 moles) of formic acid are added dropwise over 5 hours at a reaction temperature of 170° C.–200° C. A mixture of water and formic acid (a total of 150 ml) is distilled via a distillation bride during the reaction. After cooling to 80° C., 200 ml of toluene and 200 ml of water are added to the reaction mixture and stirred for 10 minutes at 80° C. The layers are separated and the organic layer is stirred with twice 100 ml of water. The toluene solution at 80° C. is cleared using 1 g of activated charcoal and 3 g of kieselguhr and evaporated to dryness in vacuo.

56 g (72.3% of theory) of 100% 4-biphenyl-imidazol-1-yl-phenyl-methane of melting 142° C. are obtained.

Known 13.6 g (0.2 mol) of imidazole are dissolved in 150 ml of acetonitrile and treated with 3.5 ml of thionyl chloride at 10° C. 13 g (0.05 mol) of 4-biphenyl-phenylcarbinol are added to the solution of thionyl-bis-imidazole thus obtained. After standing for 15 hours at room temperature, the solvent is removed by distillation in vacuo. The residue is taken up in chloroform and washed with water. The organic layer is separated off, dried over sodium sulphate, filtered and the solvent distilled off in vacuo. The oily residue is dissolved in ethyl acetate and freed from insoluble, resinous components by filtration. The solvent is once again distilled off in vacuo and the residue is purified by recrystallization from acetonitrile. 8.7 g (56% of theory) of 4-biphenyl-imidazol-1-yl-phenylmethane of melting point 142° C. are obtained.

EXAMPLE 2

19.6 g (0.1 mol) of 4-acetylbiphenylyl and 54.4 g (0.8 mol) of imidazole are heated to 170° C. to 190° C. 110.4 g (2.4 moles) of formic acid are added dropwise within 2 hours. A mixture of water and formic acid (about 50 ml) are distilled off via a distillation bridge during the reaction. Conversion (according to GC): 53.8% of 2-(4-biphenylyl)-2-imidazol-1-yl-ethane.

It will be understood that the specification and examples are illustrative but not limitative of the present invention and that other embodiments within the spirit and scope of the invention will suggest themselves to those skilled in the art.

What is claimed is:

1. A process for the preparation of an imidazolyl-methane derivative of the formula

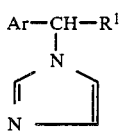

in which

Ar presents phenyl or phenyl which contains one, two or three substituents selected from the group consisting of $C_1$-$C_6$-alkyl, halogen, phenyl, phenyl substituted by halogen or $C_1$-$C_6$-alkyl phenylthio and phenylthio substituted by halogen or $C_1$-$C_6$-alkyl, phenoxy substituted by halogen or $C_1$-$C_6$-alkyl, and $R^1$ represents straight-chain or branched alkyl having up to 6 carbon atoms, phenyl or phenyl which is singly to triply, identically or differently substituted by halogen, $C_1$-$C_6$-alkyl and halogen-$C_1$-$C_6$-alkyl, wherein a ketone of the formula

Ar–CO–$R^1$ in which

Ar and $R^1$ have the abovementioned meaning, is reacted with imidazole in the presence of formic acid.

2. A process according to claim 1, in which

Ar represents phenyl or phenyl which is substituted by fluorine, chlorine, methyl, ethyl, phenyl, chlorophenyl, phenoxy or chlorophenoxy and $R^1$ represents methyl, ethyl, n-propyl, i-propyl, n-butyl tert.-butyl and phenyl or phenyl which is substituted by fluorine, chlorine, methyl or trifluromethyl.

3. A process according to claim 1, in which

Ar represents phenyl or phenyl which is substituted by chlorine or phenyl and $R^1$ represents methyl, phenyl or phenyl which is substituted by chlorine.

4. A process according to claim 1, wherein the reaction is carried out at temperatures between 100° and 250° C.

5. A process according to claim 1, wherein the reaction is carried out at temperatures between 150° and 200° C.

6. A process according to claim 1, wherein 4–12 moles of imidazole and 10–50 moles of formic acid are added per mole of ketone.

7. A process according to claim 1, wherein 6–10 moles of imdidazole and 20–40 moles of formic acid are added per mole of ketone.

8. A process according to claim 1, wherein the reaction is carried out in the presence of an acidic catalyst.

9. A process according to claim 1, wherein the reaction is carried out at temperatures between 100° and 250° C. and wherein 4–12 moles of imidazole and 10–50 moles of formic acid are added per mole of ketone.

* * * * *

UNITED STATES PATENT AND TRADEMARK OFFICE
CERTIFICATE OF CORRECTION

PATENT NO. : 4,720,549
DATED : Jan. 19, 1988
INVENTOR(S) : Zerbes et al.

It is certified that error appears in the above-identified patent and that said Letters Patent is hereby corrected as shown below:

Col. 3, line 26      Delete "36" and substitute --368--
Col. 3, line 30      Delete "bride" and substitute --bridge--

Signed and Sealed this

Twenty-sixth Day of July, 1988

Attest:

DONALD J. QUIGG

Attesting Officer      Commissioner of Patents and Trademarks